US008062662B2

(12) United States Patent
Lasic et al.

(10) Patent No.: US 8,062,662 B2
(45) Date of Patent: Nov. 22, 2011

(54) LIPOSOMES CONTAINING AN ENTRAPPED COMPOUND IN SUPERSATURATED SOLUTION

(75) Inventors: Danilo D. Lasic, Newark, CA (US); Robert M. Abra, San Francisco, CA (US); Yechezkel Barenholz, Jerusalem (IL); Tal Peleg-Shulman, Givataim (IL)

(73) Assignees: Alza Corporation, Mountain View, CA (US); Yissum Research Development Company of the Hebrew University of Jerusalem, Jerusalem (IL)

( * ) Notice: Subject to any disclaimer, the term of this patent is extended or adjusted under 35 U.S.C. 154(b) by 429 days.

(21) Appl. No.: 11/377,537

(22) Filed: Mar. 16, 2006

(65) Prior Publication Data
US 2006/0159739 A1    Jul. 20, 2006

Related U.S. Application Data

(63) Continuation of application No. 09/771,151, filed on Jan. 26, 2001, now abandoned.

(60) Provisional application No. 60/178,650, filed on Jan. 28, 2000.

(51) Int. Cl.
*A61K 9/127*    (2006.01)
(52) U.S. Cl. ............... 424/450; 264/4.1; 264/4.3
(58) Field of Classification Search .............. 424/450
See application file for complete search history.

(56) References Cited

U.S. PATENT DOCUMENTS

| 5,013,556 | A | * | 5/1991 | Woodle et al. ............ 424/450 |
| 5,252,336 | A | * | 10/1993 | Iga et al. ............ 424/450 |
| 5,631,018 | A | | 5/1997 | Zalipsky et al. |
| 5,891,468 | A | | 4/1999 | Martin et al. |
| 5,945,122 | A | | 8/1999 | Abra et al. |
| 6,110,491 | A | * | 8/2000 | Kirpotin ............ 424/450 |
| 6,348,215 | B1 | * | 2/2002 | Straubinger et al. ...... 424/450 |

FOREIGN PATENT DOCUMENTS

| EP | 0177223 | | 2/1990 |
| EP | 0 551 169 | * | 7/1993 |
| EP | 0551169 | | 7/1993 |
| WO | 98/07409 | * | 2/1998 |
| WO | WO 98/07409 | | 2/1998 |

OTHER PUBLICATIONS

Holly, R. et al., Proton Rotating Frame Spin-Lattice Relaxation Study of Slow Motion of Pore Water, J. Chem. Phys., 108 (10), 4183-4188, (1998).

Lichtenberg, D. et al., Liposomes: Preparation, Characterization and Preservation, Methods of Biochem. Analysis, Wiley (New York), 337-463, (1998).

Moeller, M. et al., Mineralization of Nanoparticles in Block Copolymer Micelles, Curr. Op. Coo. Interf. Sci., 177-187, (1997).

Roy, M. et al., The Amplitude Reduction Factor in EXAFS, J. Phys. IV France, 151-152 (1997).

Barnham, K.J. et al., NMR Spectroscopy of Platinum Drugs: from DNA to Body Fluids, Platinum and Other Metal., Plenum Press, New York, 1-16 (1996).

(Continued)

*Primary Examiner* — Gollamudi Kishore
(74) *Attorney, Agent, or Firm* — Dahna S. Pasternak; Robins & Pasternak LLP

(57) ABSTRACT

A liposome composition having a compound entrapped in a supersaturated solution and method for preparing such a composition are described.

11 Claims, 10 Drawing Sheets

OTHER PUBLICATIONS

Speelmans, G. et al., The Interaction of Anti-Cancer Drug Cisplatin with Phospholipids is Specific for Negatively Charged Phospholipids and takes Place at Low Chloride Ion Concentration, Biochim. Biophys. Acta, Elsevier Science B.V., 60-66, (1996).

Stern, E.A. et al., The UWXAFS analysis package: philosophy and details, Physica B, Elsevier Science B.V., 117-120 (1995).

Berners-Price, S.J. et al., Stereospecific Hydrogen-Bonding in Mononucleotide Adducts of Platinum Anticancer Complexes in Aqueous Solution, J.Am.Chem.Soc., 8649-8659, (1993).

Fenske, D.B., Structural and Motional Properties of Vesicles as Revealed by Nuclear Magnetic Resonance, Chem. Phys. Lipids, Elsevier Scientific Publishers Ireland Ltd., 143-162, (1993).

Gondal, J.A. et al., Comparative Pharmacological, Toxicological and Antitumoral Evaluation of Free and Liposome-encapsulated Cisplation in Rodents, Eur. J. Cancer, 29A(11), 1536-1542 (1993).

Weiss, R. B. et al., New Cisplatin Analogues in Development, Drugs, Adis International Ltd., 46(3), 143-162 (1993).

Rehr, J.J et al., High-Order Multiple-Scattering Calculations of X-Ray-Absorption Fine Structure. Phys. Rev. Lett., The American Physical Society, 69(23), 3397-3400 (1992).

Tilcock, C.P.S. et al., Lipid Polymorphism, Chem. Phys. Lipids, Elsevier Scientific Publishers Ireland Ltd., 109-125 (1986).

Appleton, T.G. et al., 15N and195 Pt NMR Spectra of Platinum Ammine Complexes: Trans- and Cis-Influence SeriesBased on 195Pt-15N Coupling Constants and 15N Chemical Shifts, Inorg. Chem., 4685-4693 (1985).

Kuroda, R. et al., Crystal and Molecular Structure of Three Isomers of Dichloradiamminedihydroxoplatinum(IV): Cis-Trans Isomerization on Recrystallization from Water, Inorganic Chem., 3620-3624 (1983).

Sur, B., et al. Effect of Liposomal Encapsulation of cis-Platinum Diamminodichloride in Treatment of Ehrlich Ascites Carcinoma, Oncology, 372-376 (1983).

A. Gabizon et al., Liposomes as in Vivo Carriers of Adriamycin: Reduced Cardiac Uptake and Preserved Antitumor Activity in Mice, Cancer Research, 4734-4739 (1982).

Faggiani, R et al., Crystalline Structure and Vibrational Spectra of cis-dichlorodiammine-trans-dihydroxo-platinum(IV),Canadian J. of Chem., 529-534 (1982).

Freise, J. et al., Pharmacokinetics of Liposome Encapsulated Cisplatin in Rats, Arch. Int. Pharmacodyn, 180-192 (1982).

C.J. Boreham, et al., A 195Pt and 15N N.M.R. Study of the Anticancer Drud, cis-Diamminedichloro-platinum(II), and its Hydrolysis and Oligomerization, Aust. J. Chem., 659-664 (1981).

Milburn, G.H.W., et al., The Crystal Structures of cis- and trans-Dichlorodiammineplatinum(II), Inorg. Phys. Theor., 1609-1616 (1966).

* cited by examiner

LIPOSOMES CONTAINING AN ENTRAPPED COMPOUND IN SUPERSATURATED SOLUTION

CROSS REFERENCE TO RELATED APPLICATIONS

The application is a continuation of U.S. application Ser. No. 09/771,151, filed Jan. 26, 2001, now abandoned; which claims the benefit of U.S. Provisional Application No. 60/178,650, filed Jan. 28, 2000, all of which are incorporated herein by reference in their entirety.

FIELD OF THE INVENTION

The present invention relates to a liposome composition and method of preparing liposomes. The liposomes of the invention have entrapped in the liposomes' aqueous core a drug in supersaturated solution, which provides the liposomes a high drug-to-lipid ratio.

BACKGROUND OF THE INVENTION

Liposomes are completely closed lipid bilayer membranes containing an entrapped aqueous volume. Liposomes may be unilamellar vesicles (possessing a single membrane bilayer) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

A primary use of liposomes is to serve as carriers for a variety of materials, such as, drugs, cosmetics, diagnostic reagents, bioactive compounds, and the like. Hydrophilic agents when entrapped in liposomes associate with the aqueous spaces in the liposome structure, primarily the internal central compartment and the spaces between lipid bilayers. Lipophilic drugs are typically associated with the lipid bilayer.

Liposome drug formulations can improve treatment efficiency, provide prolonged drug release and therapeutic activity, increase the therapeutic ratio and possibly reduce the overall amount of drugs needed for treating a given kind of ailment or disorder. For a review, see Liposomes as Drug Carriers by G. Gregoriadis, Wiley & Sons, New-York (1988).

Many methods exist for preparing liposomes and loading liposomes with therapeutic compounds. The simplest method of drug loading is by passive entrapment, wherein a dried lipid film is hydrated with an aqueous solution containing the water-soluble drug to form liposomes. Other passive entrapment methods involve a dehydration-rehydration method where preformed liposomes are added to an aqueous solution of the drug and the mixture is dehydrated either by lyophilization, evaporation, or by freeze-thaw processing method involving repeated freezing and thawing of multilamellar vesicles which improves the hydration and hence increases loading.

In general, however, passive entrapment yields a low efficiency of drug entrapment. A low drug-to-lipid ratio can be a significant disadvantage to achieving efficaceous therapy with a liposome formulation. For example, for treatment of tumor tissue, liposomes with a size of approximately 80-140 nm are required for extravasation into the tumor tissue. The small size imposes a limitation on the drug loading, especially when the drug is passively entrapped and/or when the drug has a limited solubility and/or the drug has a low affinity for the lipids. A low drug-to-lipid ratio requires administration of a large lipid dose to achieve the required drug dose.

The drug entrapment efficiency can be improved in part by using a high lipid concentration or by a specific combination of lipid components. For example, an amphiphatic amine, such as doxorubicin, may be encapsulated more efficiently into liposome membranes containing negative charge (*Cancer Res.* 42:4734-4739, (1982)). This surface electrostatic drug association with liposomes, while very stable in the test tube, leads to very rapid, almost immediate, release upon systemic administration.

Thus, loading of uncharged and non-lipophilic drugs, and in particular drugs having low solubility in aqueous phase at a sufficiently high drug-to-lipid ratio for efficaceous therapy remains a problematic issue.

SUMMARY OF THE INVENTION

In one embodiment, the invention provides a liposome containing composition having a hydrophilic compound entrapped in the liposome at a high drug-to lipid ratio. The high drug-to lipid ratio is achieved by virtue of the drug being entrapped in the liposome at a supersaturated state.

In another embodiment of the invention a method for preparing a liposome containing composition having a hydrophilic compound entrapped in the liposome in a supersaturated state is provided.

In another embodiment, the invention includes a method for preparing liposomes having a compound entrapped in a supersaturated state in the liposomes. The method includes: (i) selecting a compound having a room temperature water solubility capable of at least a two-fold increase in response to a selected condition; (ii) selecting a liposome size effective to inhibit precipitation of the compound when entrapped in a liposome; and (iii) encapsulating the compound in the liposomes.

In yet another embodiment, a compound for use in the method is capable of an increase in its water solubility at room temperature. One increase in water solubility is in response to a condition selected from the group consisting of (i) increasing solvent temperature, (ii) adding a co-solvent and (iii) changing solvent pH.

The liposomes of the invention are, in one embodiment, between about 60 to about 1000 nm in diameter. In another embodiment, liposome size is achieved by preparing liposomes having an entrapped compound at selected size intervals of between about 60 to about 1000 nm. The prepared liposomes can be analyzed microscopically, or in alternative methods, spectroscopically or via scattering techniques, such as extended x-ray adsorption fine structure, for the presence or absence of precipitated compound.

In another embodiment, a selected compound is encapsulated in liposomes by hydrating a solution of lipids with the drug solution. In another embodiment, the selected compound is entrapped by hydrating a dried lipid film with the concentrated drug solution.

In additional embodiments the liposomes may further include a lipid derivatized with a hydrophilic polymer, such as polyethylene glycol (PEG). In another embodiment, the lipids selected to form the lipid bilayer are effective to form a rigid lipid bilayer.

In another embodiment the method of the invention includes removing from an external liposome suspension medium the condition selected to maintain the drug above the room temperature solubility limit.

In another aspect, the invention includes a liposome prepared according to the method described above, where the compound is entrapped in the liposomes' central compartment in a supersaturated condition. In this aspect, the liposome composition contains a suspension of liposomes composed of a vesicle-forming lipid and a therapeutic compound entrapped in the liposomes, wherein one compound is maintained in the liposomes in a supersatured state via selection of a liposome size effective to inhibit formation of precipitated drug in the liposomes' central compartment.

The compound selected for use in a liposome is in one embodiment capable of at least a two fold increase in aqueous solubility. This increase in aqueous solubility is in response to a condition selected from the group consisting of: (i) increasing solvent temperature, (ii) adding a co-solvent and (iii) changing solvent pH.

In yet another embodiment of the invention, a method for preparing liposomes having a compound entrapped in the internal aqueous compartment in a supersaturated state is described. The method includes: (i) preparing an aqueous solution of the compound where the compound is present in the solution at a concentration above its solubility in the solution at room temperature; (ii) hydrating a lipid film or lipid solution with the concentrated drug solution to form liposomes; and (iii) sizing the liposomes to inhibit formation of precipitated compound, thereby maintaining the entrapped compound in a supersaturated solution.

In another embodiment, a selected compound is prepared such that the compound is present in an aqueous solution at a concentration above its solubility in the solution at a temperature of about 37° C.

These and other embodiments of the invention will be more fully appreciated in view of the following Detailed Description of the invention.

DETAILED DESCRIPTION OF THE INVENTION

I. Preparation of Liposomes

Figure 1A:
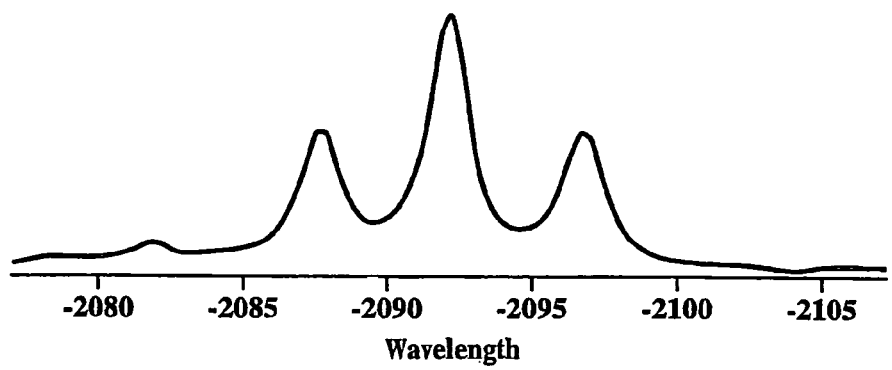
FIGS. 1A-1B are $^{195}$Pt NMR spectra of cis-Pt($^{15}$NH$_3$)$_2$Cl$_2$ with broad-band decoupling (FIG. 1A) and without broadband decoupling (Fkg. 1B)

In one aspect, the invention includes a method for preparing a liposome composition having a compound entrapped in the liposomes in a supersaturated condition. As used herein "supersaturated" includes a condition wherein a solution contains more solute than is normally necessary to achieve saturation under the same conditions. That is, the solution holds more of a dissolved solute than is required to produce equilibrium with its undissolved solute.

In another aspect, liposomes are formed by selecting a compound to be entrapped and preparing a solution having a concentration of the compound that is above the saturation concentration of the compound in water at room temperature. A solution containing the compound and having a concentration above the saturation concentration in water at room temperature can be prepared by any one of a number of methods. For example, by heating the solution to increase the solubility of the compound in the solvent, by adding a co-solvent to the aqueous solvent or by changing the pH of the aqueous solvent. This solution is referred to herein as "the concentrated solution." The procedure used to prepare the concentrated solution is, in a preferred embodiment, effective to increase the solubility of the compound in the aqueous solvent by about two-fold, preferably about three-fold, more preferably about four-fold, over the solubility of the compound in the aqueous solvent at room temperature.

Accordingly, compounds contemplated for use in the compositions and methods of the invention include compounds capable of at least about a two-fold, preferably at least about three-fold, more preferably at least about a four-fold increase in room temperature (20-25° C.) aqueous solubility via: (i) increasing solvent temperature, (ii) addition of a co-solvent, or by (iii) changing solvent pH. Preferred compounds are those with limited solubility in water at room temperature that undergo a substantial increase in solubility with increase in temperature. In the studies performed in support of the invention, cisplatin was used as the model compound. Cisplatin has a solubility at room temperature in water or saline of 1-2 mg/mL. At about 60-65° C., the solubility increases to about 8-10 mg/mL. Thus, temperature was used as the means to prepare a concentrated solution of the drug for preparation of liposomes.

Other compounds contemplated for use in the invention include therapeutic drugs such as acyclovir, gancyclovir, taxol, carboplatin and other platinum compounds and anthraquinones, such as doxorubicin, epirubicin, daunorubicin and idarubicin, as well as poorly water-soluble antibiotics, proteins and peptides.

Continuing the description of a method for preparing lipid vesicles, in a separate container, lipids can be selected to provide a desired lipid vesicle composition and dissolved in a suitable solvent. Lipids suitable for formation of lipid vesicles are known to those of skill in the art. See, for example, U.S. Pat. No. 5,013,556 at Col. 9, lines 34-62, and U.S. Pat. No. 5,891,468 Col. 7 line 5 bridging to Col. 8, line 48. Lipid components used in forming the liposomes are selected from a variety of vesicle-forming lipids, and are typically phospholipids and sterols. The lipids can be selected to achieve a more fluidic lipid bilayer via selection of lipids with acyl chains that are relatively unsaturated, thereby to achieve a lipid bilayer having a relatively higher permeability to entrapped compound than a more rigid bilayer. More rigid lipid bilayers are formed using highly saturated phospholipids in order to form lipid bilayers with a lower permeability of entrapped compound. In another embodiment of the invention, liposomes that contain a lipid derivatized with a hydrophilic polymer chain, such as polyethylene glycol or other polymers, are described, for example, in U.S. Pat. Nos. 5,013,556 and 5,631,018.

The composition of the lipid bilayer is selectively varied according to the drug selected for entrapment. Drugs having a higher permeability in lipid bilayers are better retained in the liposomes by forming a lipid bilayer with saturated or lipid rigidifying components. Drugs that are not readily permeable through lipid components in lipid bilayers can be entrapped in liposomes formed with fluidic lipid components.

The selected lipid components, as described above, can be dissolved in a suitable solvent. The lipids are hydrated with the concentrated solution of drug to form liposomes. In detailed studies described throughout the specification, a concentrated solution of cisplatin was used to hydrate an ethanolic solution of lipids, (Example 1). It will be appreciated by those of skill in the art that the concentrated drug solution can also be used to hydrate a dried lipid film, where the solvent solubilizing the lipids is removed to leave a dried lipid film for hydration (see for example, U.S. Pat. No. 5,013,556 Col. 10, lines 60-65. After hydration, the lipid-drug mixture is mixed for a time sufficient for liposome formation.

The liposomes are sized to a specific size via one of several methods known in the art, such as sonication, homogenization or extrusion. Typically, a liposome size is selected to inhibit formation of precipitate in the liposomes' central compartments when conditions of the liposome composition are altered to reduce the solubility of the drug in the concentrated solution. Such a size is determined by preparing several liposome compositions having different sizes, altering a condition that maintains the increased drug concentration and analyzing the liposomes for the presence of drug precipitate. As used herein, "precipitate" or "precipitation" is intended to include a drug in any form, such as a crystalline form, semisolid form or an amorphous form drug. Liposomes having a size such that no drug precipitate is present are within the scope of the invention.

Typically, liposomes having a size of between about 60-1,000 nm are suitable, preferably a size of between about 70-500 nm. Analysis of the liposomes for the presence of drug precipitate can be performed, for example, by visualization via microscopy (electron microscopy or high resolution cryo-electron microscopy) or by various spectroscopic techniques, including for example, IR, Raman, NMR or by scattering techniques such as Extended x-ray absorption fine structure (EXAFS).

The liposomes are typically sized to a size selected to inhibit formation of precipitated drug. This typically occurs when the condition which maintains the drug at a concentration above the solubility of the drug in water at room temperature is altered in the exterior phase of the liposome suspension. For example, if an increase in temperature was used to increase the solubility of the drug for preparation of the concentrated drug solution, the temperature of the liposome suspension is lowered. If an increase or decrease in pH was used to increase the drug solubility, the pH is adjusted to the final desired pH. If a co-solvent was added to the concentrated drug solution to increase the drug solubility, the co-solvent is removed from the external liposome phase via a selected method, such as diafiltration, density gradient centrifugation, dialysis, distillation, vacuum removal, and the like.

II. Characterization of the Liposomes

As described above, the invention provides efficient and stable encapsulation of drugs having limited water solubility at room temperature. Such compounds are known to be difficult to entrap in liposomes in a drug-to-lipid ratio useful for therapy. In the studies performed in support of the invention, the anti-cancer agent cisplatin was used as an exemplary drug. It should be appreciated, however, that the composition and method of the invention are contemplated for use with a variety of compounds, which have limited water solubility at room temperature, and other exemplary drugs are described above.

Cisplatin (cis-diamminedichloroplatinum(II)), is a heavy metal complex containing a central atom of platinum surrounded by two chloride atoms and two ammonia molecules in the cis position. Cisplatin is widely used for treating a variety of solid tumors, including testicular, head and neck, and lung tumors. Like other cancer chemotherapeutic agents, cisplatin is a highly toxic drug. The main disadvantages of cisplatin are its extreme nephrotoxicity, which is the main dose-limiting factor, its rapid excretion via the kidneys, with a circulation half life of only a few minutes, and its strong affinity to plasma proteins (Freise, J., et al, Arch. Int. Pharmacodyn., 258:180-192 (1982)). Encapsulation of cisplatin in liposomes as an approach to overcoming toxicity has been described for example in Abra, et al., U.S. Pat. No. 5,945,122; Gondal, J. A., et al., Eur. J. Cancer, 29A(11):1536-1542 (1993); Sur, B., et al., Oncology, 40:372-376 (1983); Weiss, R. B., et al., Drugs, 46(3):360-377 (1993). Cisplatin is typically difficult however, to efficiently entrap in liposomes because of the drug's low aqueous solubility, approximately 1-2 mg/mL at room temperature, and low lipophilicity, both of which contribute to a low drug/lipid ratio.

In accordance with the invention, liposome-containing cisplatin in a supersaturated state was prepared as described in Example 1. Briefly, an aqueous solution of the drug was prepared with the drug at a concentration above its solubility limit in the solution at room temperature, about 20-25° C., at pH=7. In this case, the solubility of the drug was increased by heating the temperature of the solution. Other methods to increase the solubility of a drug in an aqueous solution at room temperature, as discussed above, are also suitable. The prepared solution is subsequently used to hydrate lipids selected for formation of the liposome lipid bilayer, thereby forming liposomes containing the supersaturated drug solution in the central core compartment of the liposomes. More specifically, and in the particular case using cisplatin, the liposomes contained cisplatin entrapped at a concentration of about 8 mg/ml, about four times above cisplatin solubility at room temperature (1-2 mg/mL). The liposomes were sized by extrusion to an average mean particle diameter of 106 nm.

The liposomes containing cisplatin at 8 mg/ml were characterized by NMR and by extended X-ray absorption fine structure (EXAFS), as will now be described.

A. Characterization by NMR

NMR is a powerful tool for evaluation of liposomal formulations since the anisotropic nature of molecular motion within the lipid bilayers and the anisotropy of the membrane structure can be evaluated by this technique [Fenske, P. B., *Chem. Phys. Lipids* 64:143, (1993); Tilcock, C. P. S., *Chem. Phys. Lipids* 40:109, (1986)]. For cisplatin-loaded liposomes, NMR provides information on both the liposome phospholipids (physical state, rate of motion) and on the platinum complex (oxidation state and coordination sphere). The combination of NMR and atomic absorption spectrometry can be used to quantify the amount of soluble platinum in the liposome formulations.

Liposomes containing $^{15}$N-labeled cisplatin were prepared as described in Example 2. The drug loading was performed at a temperature of between 60-65° C. to increase the cisplatin solubility to about 8 mg/mL. After formation of large unilamellar vesicles, the temperature of the liposome suspension was lowered to 4° C. at which the drug solubility is about 1-2 mg/mL.

1. Analysis by $^{195}$Pt NMR $^{195}$Pt NMR spectroscopy provides information on the oxidation state of the metal and on the nature of the four ligands in the platinum's first coordination sphere. This is due to the fact that the chemical shift range of Pt complexes spans several thousand ppm and that the chemical shift is sensitive to both the oxidation state of the Pt (II and IV) and to the nature of the atom which is bound to the Pt.

Figure 1B:
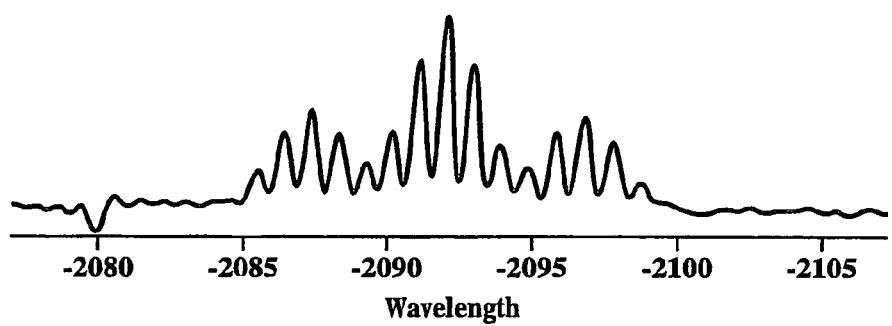

The cis-Pt($^{15}$NH$_3$)$_2$Cl$_2$, prepared as described in Example 2A, was characterized by $^{195}$Pt NMR spectroscopy and the spectrum is shown in FIGS. 1A-1B. As seen in FIG. 1A, the broad-band decoupled spectrum shows the expected triplet due to the coupling of two equivalent $^{15}$N atoms. When the broad-band decoupling was turned off, each of the three $^{195}$Pt resonances was split to a septet by the six equivalent hydrogens, as seen in FIG. 1B.

Figure 2:
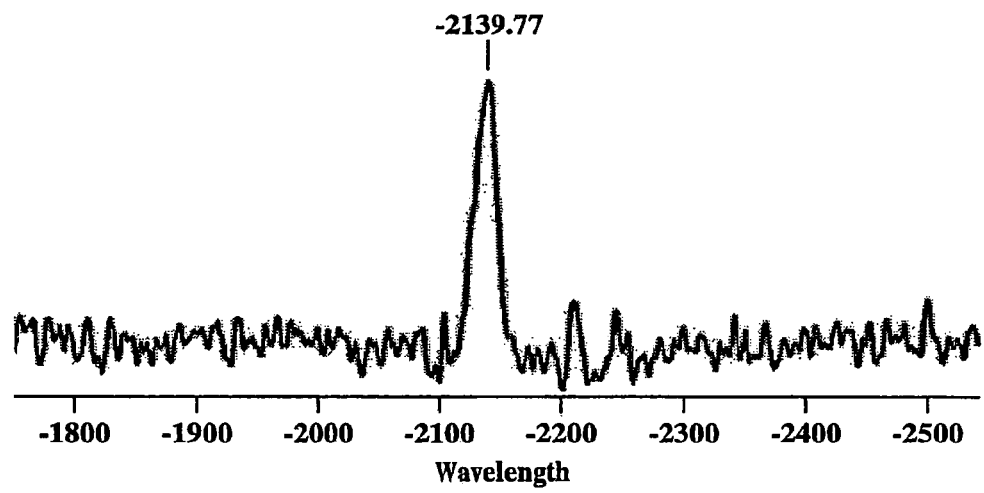
FIG. 2 is a $^{195}$Pt NMR spectrum of cisplatin encapsulated in liposomes.

$^{15}$Pt NMR measurements of cisplatin containing liposomes clearly show a single chemical shift (range −1350 to −2700 ppm) at −2139.7 ppm, as seen in FIG. 2. This indicates that the cisplatin is mainly (>90%) one species of Pt(II), which is the intact cisplatin. No additional platinum peaks were detected, indicating that no other platinum species, i.e., platinum tri- or tetra-amine, were formed, though adducts of Pt(II) with large molecules would not be observed by $^{195}$Pt NMR. Pt(II) can undergo a two-electron disproportionation to give solid Pt(O) and soluble Pt(IV) complexes, especially when they are heated in non-acidic solutions. No black precipitate was detected in the samples, suggesting that no Pt(O) was present, and no peaks were observed in the $^{195}$Pt NMR in the region between +1000 to −500 ppm, indicating that no Pt(IV) complexes were present in the solution.

Figure 3A:
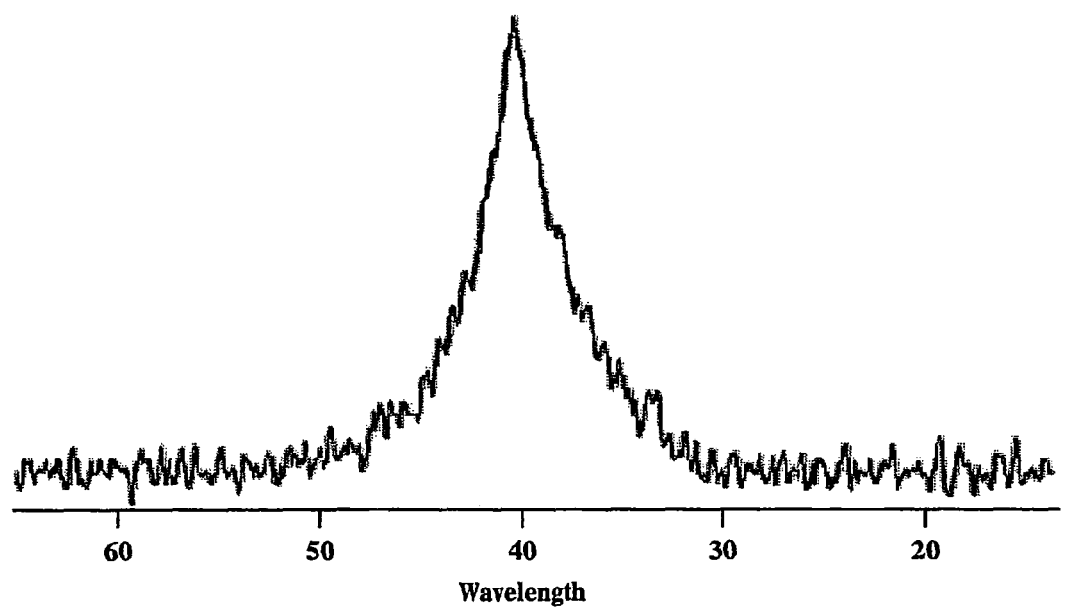
FIGS. 3A-3B are $^{31}$P NMR spectra of cisplatin-containing liposomes (FIG. 3A) and of control, placebo liposomes (FIG. 3B)
Figure 3B:
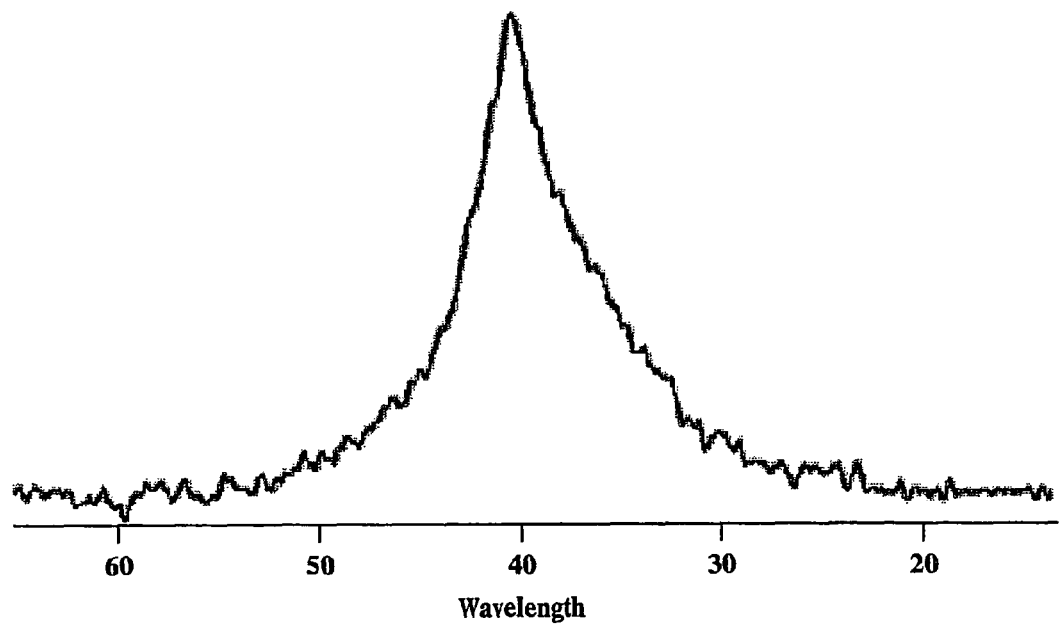

2. Analysis by $^{31}$P NMR $^{31}$P NMR was used to verify the state of phospholipids in the lipid vesicles, as well as to verify the homogeneity of liposomal preparations with respect to size distribution and the number of lamellae. The $^{31}$P NMR spectra of the liposome formulations for which samples were also measured by $^{195}$Pt NMR are described in Table 1 were measured; they displayed the slightly asymmetric peaks typical of phospholipid vesicles. The same samples were measured by $^{95}$Pt NMR to verify their platinum content. At room temperature, the $^{31}$P peak observed was very broad. This is in agreement with previous data of vesicles composed of saturated phospholipids and cholesterol below the gel-to-liquid crystalline phase transition temperature™ of the matrix lipids (Tm=52.5° C. for hydrogenated phosphatidylcholine) (Lichtenberg D. et al., METHODS OF BIOCHEMICAL ANALYSIS, D. Glick, Ed., Vol. 23, Wiley, New York, p. 337 (1998)). As seen in FIGS. 3A-3B, at 60° C., above the Tm, sharp $^{31}$P spectra were observed for both the platinum containing (FIG. 3A) and control (FIG. 3B) liposomes. At 60° C., approximately 10 scans were sufficient to produce reliable data with a high signal-to-noise ratio. Peak analysis revealed somewhat asymmetric peaks for both (skewness to the right), as is expected for phospholipid vesicles. Measurement of the linewidths at half the height can serve as a criterion for the interaction of the platinum with the phospholipids in the formulation. Linewidths at half the height ($\Delta v_{1/2}$) were determined at 60° C., and values of 6.3 ppm and 4.2 ppm were obtained for the control and for cisplatin-liposomes, respectively. Comparison between the Pt-containing liposomes and the control liposomes indicated minor interactions between the platinum and the phospholipids. A weak interaction may occur, as $\Delta v_{1/2}$ Pt-liposomes $<\Delta v_{1/2}$ control, although both vesicles are of similar size. The data are in good agreement with $^{31}$P measurements of 100-200 nm diameter LUV (i.e. ~5 ppm for egg PC/DSPG 85/15 $\Delta v_{1/2}$) [Tilcock, C. P. S., *Chem. Phys. Lipids* 40:109 (1986)]. The linewidth suggests no major contamination with MLV. Thus, $^{31}$P NMR has shown by the shape of the peaks that there are no phospholipids in a hexagonal type II state.

TABLE 1

Liposome Formulations for $^{31}$P and $^{195}$Pt Spectroscopy

| Formulation | P (mg/mL) | Phospholipid (mM) | total lipids (mg/mL) | Pt (mg/mL) | size (nm) |
|---|---|---|---|---|---|
| placebo-lipo | 2.65 | 86 | 109 | — | 104 |
| cisplatin-lipo | 9.75 | 315 | 403 | 1.8 | 116 |

3. Analysis by Heteronuclear Single Quantum Coherence (HSQC)

While $^{195}$Pt NMR spectroscopy provides information on the oxidation state of the Pt complex and on the nature of atoms in the first coordination sphere, it cannot distinguish between a water ligand, a carboxy ligand or a phosphate ligand, since they all bind the Pt through an oxygen atom. $^{15}$N NMR spectroscopy has been used in conjunction with $^{195}$Pt NMR spectroscopy to provide the missing information Barnham, K. J., PLATINUM AND OTHER METAL COORDINATION COMPOUNDS IN CANCER CHEMOTHERAPY 2, Pinedo, H. M., etal. (Eds.), Plenum Press, New York, p. 1-16 (1996); Berners-Price, S. J., *J. Am. Chem. Soc.* 115:8649 (1993). The $^{15}$N chemical shift and the $^{15}$N—$^{195}$Pt coupling constants are sensitive to the ligand that is trans to the $^{15}$N [Appleton, T. G., et al., *Inorg. Chem.* 24:4685 (1985)]. The lack of $^4$N causes the $^{195}$Pt resonance to be sharp, and the coupling constants ($^{195}$Pt—$^{15}$N, $^{195}$Pt—$^1$H) can be obtained. $^{15}$N-labeled cisplatin [cis-Pt($^{15}$NH$_3$)$_2$Cl$_2$] is readily prepared as described in Example 2, however, the low sensitivity of $^{15}$N NMR prevents its use for monitoring the Pt complexes in these experiments.

Inverse detection experiments detect the protons that are coupled to $^{15}$N and thus provide information about the chemical shifts and coupling constants of the $^{15}$N which depend on the ligands in the first coordination sphere of the Pt and on its oxidation state. The main advantage of using $^{15}$N-labeled cisplatin is the ability to apply heteronuclear single or multiple quantum coherence (HSQC or HMQC, respectively) NMR techniques. HSQC and HMQC are two-dimensional inverse detection experiments that have the proton chemical shifts on one axis and the $^{15}$N chemical shifts on the second axis. HSQC and HMQC of $^{15}$N-labeled Pt complexes have been used successfully, to detect micromolar concentrations of Pt complexes. In the studies performed in support of the invention, HSQC was used, since it gives narrower lines and better resolution than HMQC. In a typical HSQC experiment micromolar concentrations of cisplatin in approximately 20 minutes were observed. In addition to the tremendous gain in sensitivity, HSQC selectively detects only the protons that are coupled to the $^{15}$N, thus ignoring all the other protons in the solution (from the liposomes) and simplifying the interpretation of the data.

Figure 4A:
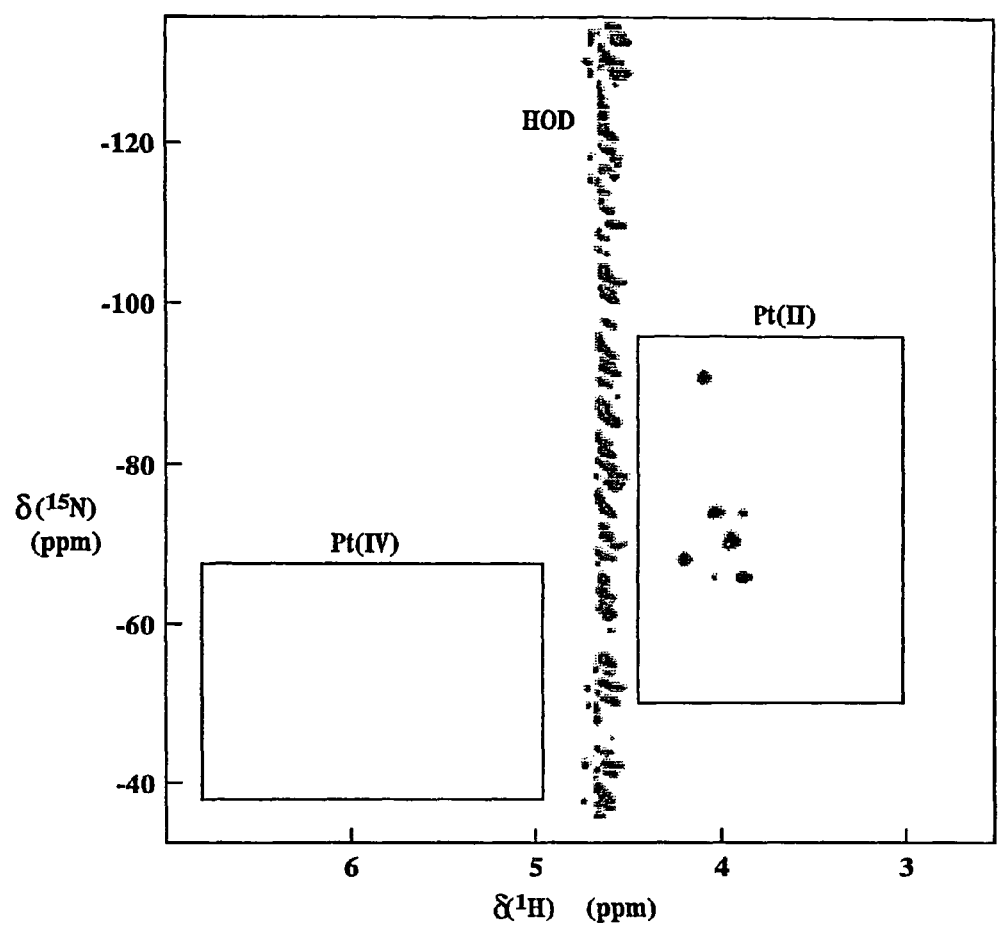
FIGS. 4A-4B are spectrum obtained by heteronuclear single quantum coherence spectroscopy of cis-Pt($^{15}$NH$_3$)$_2$Cl$_2$ in water (FIG. 4A) and an enlargement of region I(b((FIG. 4B)
Figure 4B:
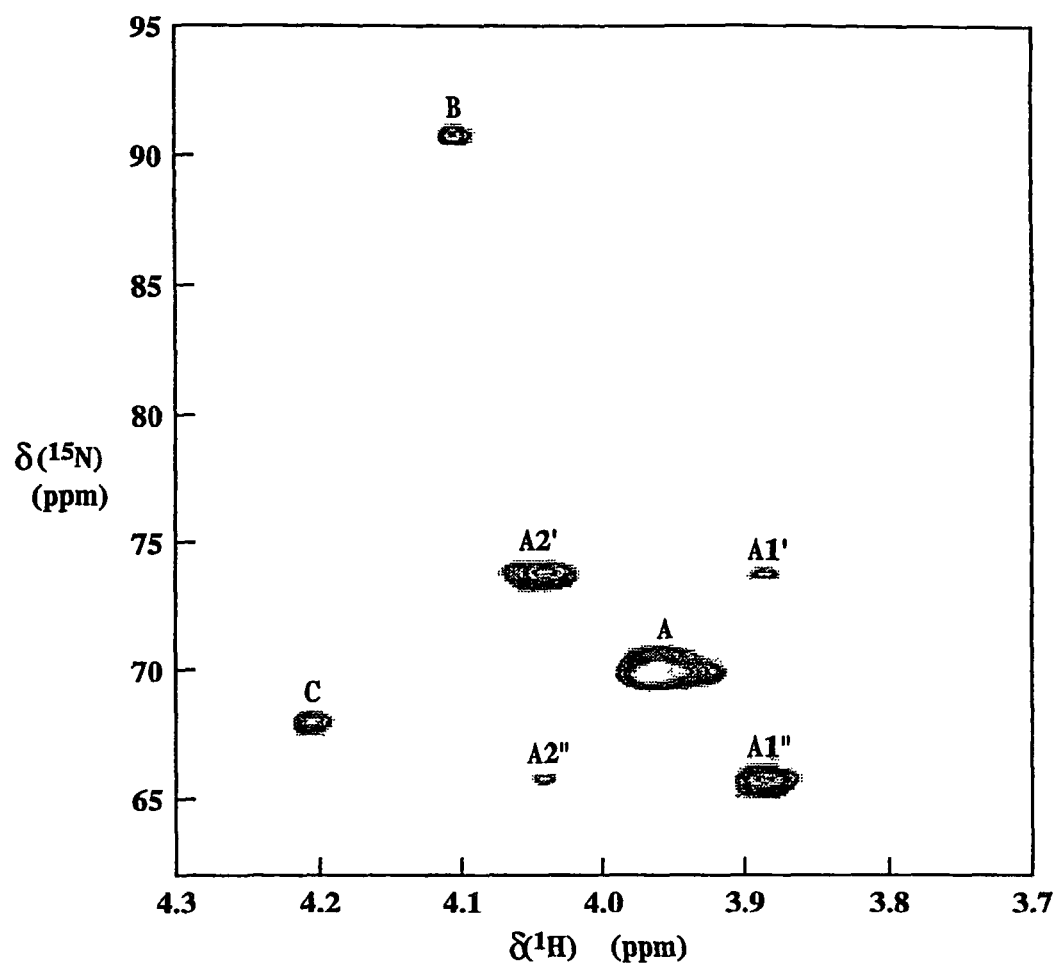

The HSQC of cis-Pt($^{15}$NH$_3$)$_2$Cl$_2$ in water is depicted in FIGS. 4A-4B. The correlation peaks are located in region I, which is characteristic of Pt(II) complexes. There are no peaks in region II, where the Pt(IV) peaks are expected (Barnham, K. J., PLATINUM AND OTHER METAL COORDINATION COMPOUNDS IN CANCER CHEMOTHERAPY 2, Pinedo H. M., et al. (Eds.), Plenum Press, New York, p. 1-16 (1996)). An enlargement of region I is shown in FIG. 4B which shows that there are three peaks (A, B, and C) and each peak has additional satellites (A1', A1", A2' and A2"). Peak A belongs to cis-Pt($^{15}$NH$_3$)$_2$Cl$_2$, where the two equivalent nitrogens give rise to a single peak. Peaks B and C belong to a single complex of cis-[Pt($^{15}$NH$_3$)$_2$Cl (H$_2$O)]$^+$ where peak B is ascribed to the nitrogen that is trans to the aqua ligand, and peak C, to the nitrogen that is trans to the chloride ligand. The $^{195}$Pt—$^{15}$N coupling constants can be measured from the distance between A1' and A1", and the $^{195}$Pt—$^1$H coupling constants can be measured from the distance between A1" and A2". The hydrolysis reaction of cisplatin, which is known to occur in aqueous solutions, is not easily observed by $^{195}$Pt NMR but is easily observed by HSQC.

Figure 5:
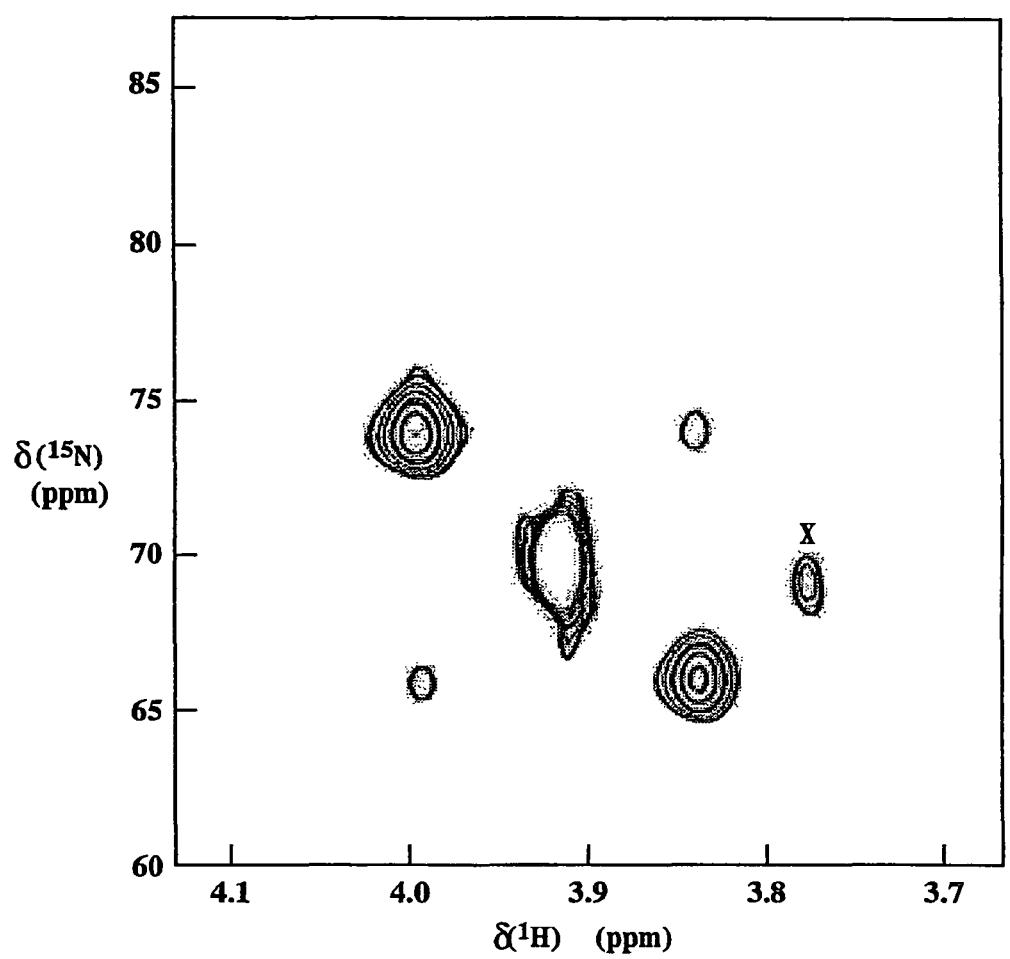
FIG. 5 is a spectrum obtained by heteronuclear single quantum coherence spectroscopy of cis-Pt($^{15}$NH$_3$)$_2$Cl$_2$ following encapsulation in liposomes; the peak denoted by "x" is unidentified.

HSQC spectra of cis-Pt($^{15}$NH$_3$)$_2$Cl$_2$ passively encapsulated in the aqueous phase of approximately 100 nm LUV appear almost identical to the spectrum of the native drug. However, there is one small difference: the distance between the satellite peaks is somewhat smaller than in the parent compound. This may be related to the interaction of the cis-Pt($^{15}$NH$_3$)$_2$Cl$_2$ with the lipids, or to the rather low "activity" of the water inside the liposomes. The latter is supported by the lack of peaks attributed to the aqua species, which are clearly visible in the spectrum of the native drug. Furthermore, as seen in FIG. 5, the spectrum of the cisplatin-encapsulated liposomes does not have any peaks in the Pt(IV) region, indicating that the process of the encapsulation of cis-Pt($^{15}$NH$_3$)$_2$Cl$_2$ into the liposomes did not cause disproportionation of the cisplatin. In addition, the lack of $^{15}$NH$_4^+$ peak in the spectrum suggests that no deamination (loss of the $^{15}$N ligand) occurred and that all the Pt(II) complexes can be accounted for by the HSQC experiment. Thus, it is safe to conclude that the only Pt species in the encapsulated liposomes are cisplatin and some cis-[Pt($^{15}$NH$_3$)$_2$Cl(H$_2$O)]$^+$. An unidentified peak (marked as 'X') is visible in the spectrum, and HPLC chromatograms of these samples detected only very minor impurities (<5%) (results not shown).

Figure 6:
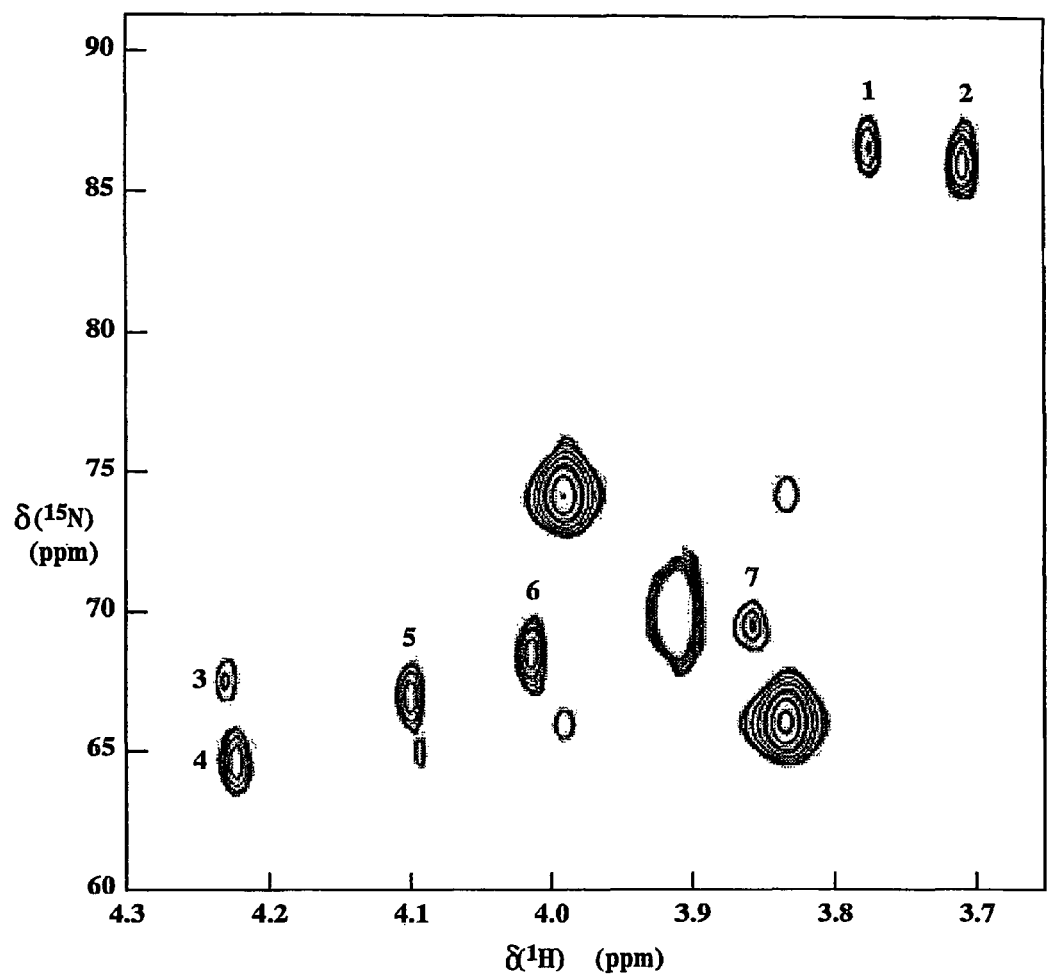
FIG. 6 is a spectrum obtained by heteronuclear single quantum coherence spectroscopy of cis-Pt($^{15}$NH$_3$)$_2$Cl$_2$ following encapsulation in the presence of a histidine buffer where peaks 1-7 are attributed to cis-Pt($^{15}$NH$_3$)$_2$Cl$_2$-histine species.

The final formulations with the cisplatin included a histidine buffer. $^1$H—$^{15}$N-HSQC NMR is sensitive enough to detect even the slightest impurities in the sample. Such impurities were observed when histidine buffer was present during a process identical to the liposome preparation but in the absence of lipids (no encapsulation) or when the histidine buffer that was present in the process of platinum encapsulation in the liposomes. As seen in FIG. 6, the $^1$H—$^{15}$N-HSQC spectra measured revealed peaks additional to those of the $^{15}$N-labeled compound. Any cisplatin-histidine species detected are attributed to aqueous cisplatin during encapsulation in the liposomes.

Figure 7:
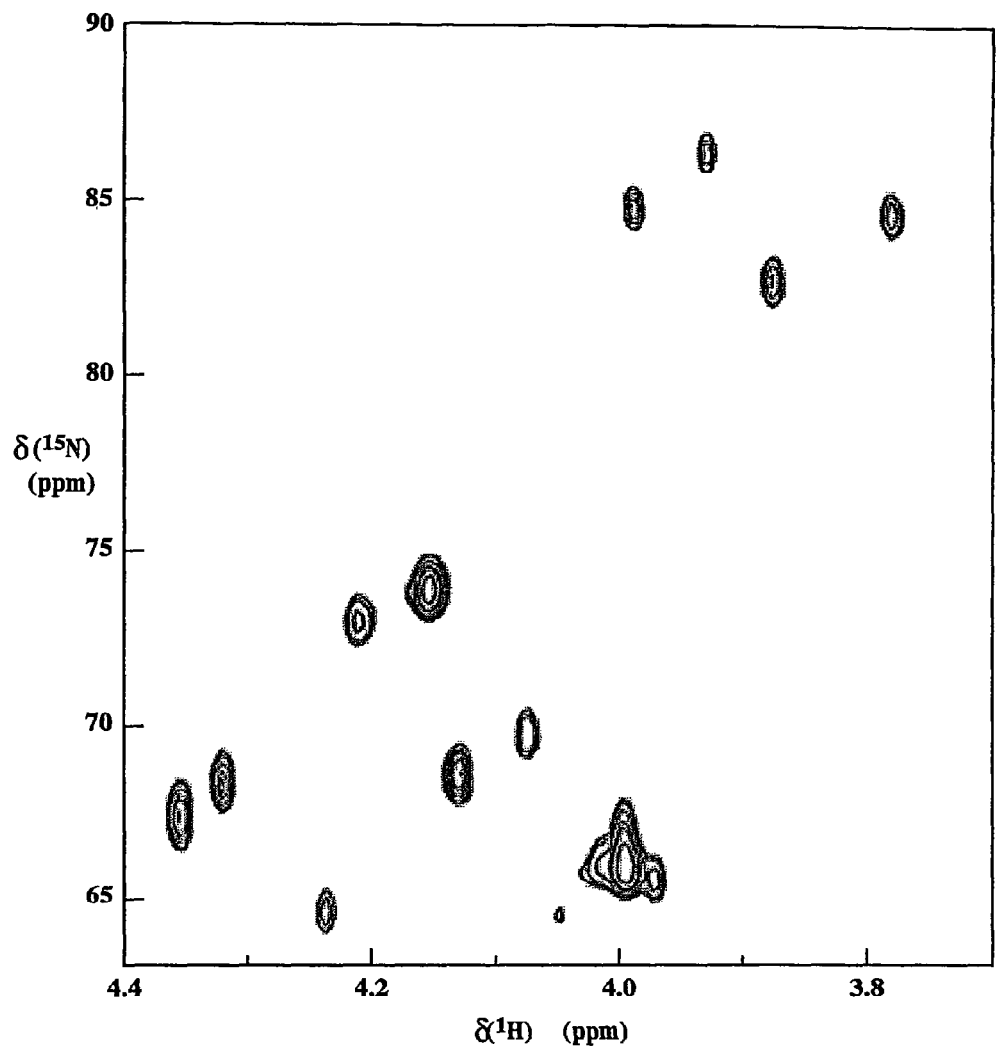
FIG. 7 is a spectrum obtained by heteronuclear single quantum coherence spectroscopy of cisplatin following incubation with N-acetyl-histidine.

Further experiments with known quantities of the amino acid histidine indicated that these foreign peaks could be attributed to binding of the drug to the histidine in the buffer during the encapsulation process. These associations are irreversible, thus making the drug unavailable, once bound. The reactivity of the $^{15}$N-labeled cisplatin towards biological buffers was examined using carboxy groups of the N-acetyl-histidine, in order to assess the contribution of the histidine amino group. Following 24-hour incubation of a 1:1 mole ratio of $^{15}$N-cisplatin and N-acetyl histidine, various new peaks appeared, probably belonging to cisplatin-histidine species, as seen in FIG. 7. These results were further verified by means of HPLC; the chromatograms obtained indeed verified the presence of a cisplatin-histidine species (approximately 20-30% of the platinum detected) (results not shown).

A similar study was carried out with N-BOC-methionine. This study suggested that in cisplatin-encapsulated liposomes in which the encapsulation was performed the absence of histidine buffer and the histidine is added after the encapsulation process is finished, as described in Example 1 (FIG. 5) there is no contact between the histidine buffer and $^{15}$N-cisplatin, resulting in liposomes which are non-leaky and very stable. The study further demonstrated that there was no leakage of the $^{15}$N-labeled cisplatin from the liposomes, as peaks belonging to cisplatin-histidine species were not observed.

4. Quantification of Platinum Content by $^{195}$Pt NMR

Other parameters to be determined regarding the platinum encapsulated in the liposomes include the drug-to-lipid ratio, and how much of the liposomal drug is behaving like water-soluble cisplatin. In the case of cisplatin, it is expected that only the soluble portion of the platinum within the liposome will be discharged and able to act upon cellular DNA; any platinum precipitate may be considered as unavailable drug. Thus, a comparative study carried out using an internal reference of K$_2$PtCl$_4$ indicated that, unlike atomic absorption spectroscopy, it was possible to use $^{195}$Pt NMR measurements to quantify selectively only the soluble cisplatin and thus obtain a clear indication as to the physical state of the platinum contained in the liposomes. Any platinum in the solid state (i.e., in a precipitate or even in a suspension of very fine particles) would be undetected; its T$_2$ would be very short, broadening the lines to such an extent that they would disappear into the baseline.

The liposome samples were measured at both 37° C. and 60° C. in order to observe the effect of the rise in temperature on the solubility of the platinum in the liposomes. The rise in temperature did not increase the observed peak areas; however, very small peaks of the aqua species were detected at 60° C. This agrees with the data obtained in the HSQC NMR measurements discussed above.

The four liposome samples used in this part of the study are described in Table 2 and are of somewhat varying size and lipid concentration. These factors may influence the viscosity of the sample and therefore contribute to broader line widths in the NMR spectrum. A significant difference between samples of soluble cisplatin in water and the liposome cisplatin samples was not observed. When measured at 60° C., lines were broader, which is consistent with a shorter T$_2$ and a rapidly decaying signal. A direct correlation between the liposome size and the line width of the cisplatin peak was found; as the liposome size increased, so did the width of the cisplatin peak. An inverse correlation existed between the lipid concentration and the width of the cisplatin peak: the line width increased as the lipid concentration decreased.

TABLE 2

Liposomal Formulations For [$^1$H,$^{15}$N] HSQC NMR Spectroscopy

| Parameter | Sample 1 | Sample 2 | Sample 3 | Sample 4 |
|---|---|---|---|---|
| Size (nm) | 112 | 125 | 100 | 107 |
| cis-Pt (mg/mL) | 1.0 | 1.0 | 0.9 | 0.9 |
| Lipid (mM) | 104 | 89 | 110 | 110 |
| External Phase | 10% sucrose 1 mM NaCl 10 mM histidine pH 6.5 | 0.9 NaCl 10 mM histidine pH 6.5 | 3% sucrose 3.3% NaCl 10 mM histidine pH 6.5 | 3% sucrose 3.3% NaCl 10 mM histidine pH 6.5 |
| Comment | | | never frozen | frozen and thawed |

The liposomes for use in this study were prepared in the presence of ethanol during the first stages of liposome formulation and a study was performed to determine the effect of ethanol on the solubility of cisplatin. Hence, the solubility of cisplatin at 1 and 8 mg/ml at room temperature and at 65° C. in 0.9% NaCl and in 20% ethanol in 0.9% NaCl was examined. At 1 mg/ml, cisplatin was soluble under all conditions, while at 8 mg/ml, most of the cisplatin precipitated at room temperature, yet was mostly soluble at 65° C. Lowering the temperature back to room temperature led to the precipitation of most of the 8 mg/ml of the cisplatin, in both the absence and presence of 20% ethanol. Thus, it can be concluded that the presence of 20% ethanol did not improve the solubility of cisplatin. NMR measurements indicate that the solubility of free cisplatin in the aqueous phase is limited to ~2 mg/ml, and is increased upon a rise in temperature to 60° C. The NMR experiments show detection of a peak whose integration is proportional to ~2 mg/ml, whereas the insoluble platinum precipitate is in fact undetected. In the case of the liposomes, nearly all the cisplatin accounted for by atomic absorption is soluble in the intraliposomal aqueous phase, which suggests that the intraliposomal concentration is higher than 2 mg/ml, which is the solubility at room temperature. It was found that in spite of the fact that the concentration of cisplatin during liposome preparation was above the solubility at room temperature (or 4° C.), nearly all the cisplatin in the liposomes behaved as if soluble in the intraliposomal aqueous phase. From the solubility studies it is clear that ethanol is not responsible for the higher than expected drug-to-lipid ratio.

The NMR studies have shown that cisplatin remains intact during loading into the liposomes and that the encapsulated cisplatin resemble, with minor differences, the parent compound dissolved in the aqueous phase. All the cisplatin present in the liposomes behaves like a water-soluble drug, and there is no suggestion of an insoluble drug. The drug within the liposomes does not precipitate. This fact is further confirmed by the EXAFS study described below.

B. Characterization by Extended X-ray Absorption Fine Structure (EXAFS)

Extended X-ray Absorption Fine Structure (EXAFS) provides information on local structure of selected atoms in a sample. In the method, the scattering of a photoelectron, emitted in the process of x-ray photoeffect, is exploited to scan the immediate atomic neighborhood. The interference pattern, resulting from the scattering, is resolved as a small oscillation of the x-ray absorption coefficient on the energy or photoelectron wavenumber scale. The effect is resolved only for slow photoelectrons, ie., immediately above any of the x-ray absorption edges. Hence, the selectivity of the method with regard to the target atom. From the amplitude, phase and period of the oscillations, most readily retrieved by Fourier transform of the data, the number, species and distance of the neighbor atoms can be deduced. Further analysis can also provide the degree of thermal and/or structural disorder, so that materials in crystalline as well as various amorphous states can be studied.

For platinum, the L3 absorption edge falls into the energy region where best resolution of monochromators for synchrotron radiation can be expected. Thus, Pt L3-edge EXAFS spectra were measured on the liposome encapsulated cisplatin to determine the local structure around Pt atoms in the sample. The system was studies in the liquid, frozen and freeze dried state. For comparison, Pt L3-edge EXAFS of free drug in solid and dissolved form were also measured.

Figure 8:
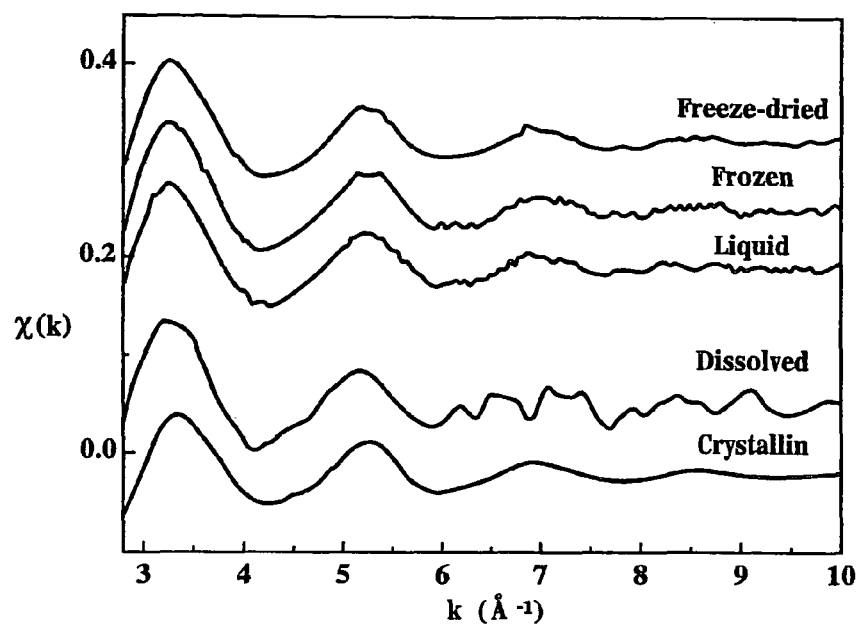
FIG. 8 is a $k^2$-weighted Pt L3-edge extended x-ray absorption fine structure (EXAFS) spectra of crystalline cisplatin, dissolved cisplatin and three liposome-encapsulated cisplatin samples (liquid, frozen and freeze-dried). The spectra are shifted vertically for clarity and the best of the data (represented by the dots) is represented by the solid line.
Figure 9:
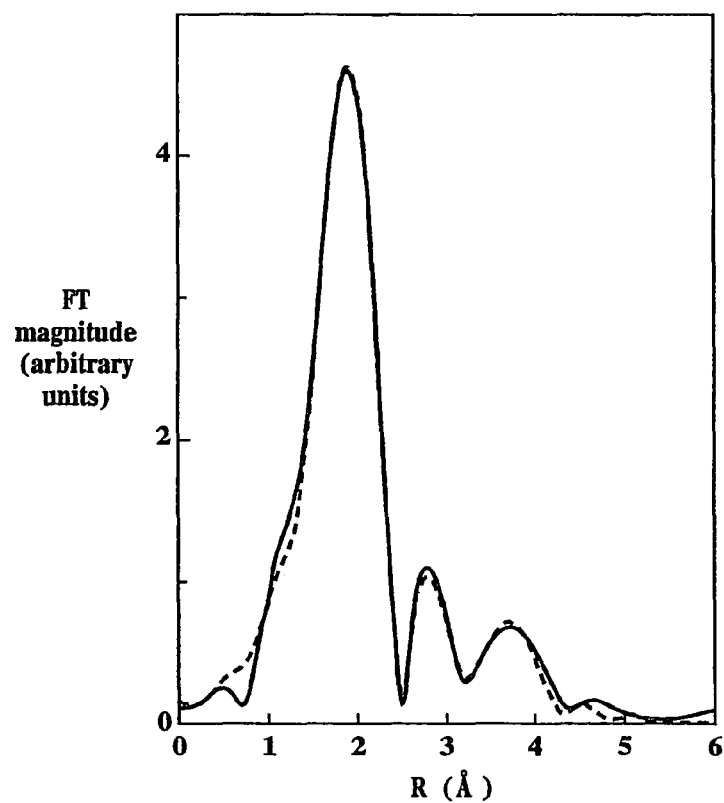
FIG. 9 is the $k^2$-weighted Fourier transform of the EXAFS spectrum of crystalline cisplatin, where the solid line represents the experimental data and the best fit model function is represented by the dashed line.

Standard k2-weighted EXAFS spectra $\chi(k)$ at the Pt L3 edge for crystalline and dissolved cisplatin and for three liposome-encapsulated cisplatin samples (liquid, frozen and freeze-dried), prepared as described in Example 3, are shown in FIG. 8.

FIGS. 8-13 are Fourier-transformed $k^2$-weighted EXAFS spectra, calculated in the k interval 3 Å$^{-1}$ to 12 Å$^{-1}$ for the individual samples shown in FIG. 8. The peaks in the spectra correspond to consecutive shells of atoms, neighbors to the Pt atom. Structural parameters are quantitatively resolved from these spectra by comparing the measured signals with model signals, constructed ab initio from the set of scattering paths of the photoelectron in a tentative spatial distribution of neighbor atoms with the FEFF6 programme code [Rehr, J. J., et al., *Phys. Rev. Lett.* 69:3397 (1992)]. In the same way, the atomic species of a neighbor is recognized by its specific scattering phase shift.

In the initial step, the signal of the crystalline cisplatin sample is analyzed. Although it is not directly relevant for the study of the encapsulation effects, its high-quality signal serves as a benchmark of the achievable resolution. Most importantly, crystallographic data can be used to build a model of the neighborhood of the Pt atom (Milburn, G. H. W., et al., *J. Chem. Soc. A. JCSIA*, p. 1609 (1966)). Indeed, a perfect agreement is found for the signal of the first-shell N and Cl neighbors at 2.05 Å and 2.33 Å respectively. Both species are identified unambiguously together with their occupation number of 2.

Further structure in the FT spectrum between 2.4 and 4.0 Å can be completely explained by the contribution of higher order scattering on the first shell neighbors, and of the scattering on the second shell of neighbors, comprising two Pt at 3.37 Å, as suggested by the crystallographic data (Milburn, G. H. W., et al., *J. Chem. Soc. A. JCSIA*, p. 1609 (1966)). However, the contributions of further Cl and N neighbors at about the same distance, predicted by the crystallographic model cannot be accommodated. Apparently, the measurement and the model refer to different crystal modifications. In this way, the closest neighbors, the N and Cl atoms of the cisplatin molecule itself and the closest Pt atoms of adjacent molecules would be found in their predicted positions, while further neighbors, brought into the vicinity of the Pt atom by the particular stacking of molecules within the crystal, would not. For the neighborhood thus constructed and refined with the best fit of the data in the k region of 3 Å$^{-1}$-12 Å$^{-1}$ and the R region of 1.1 Å-4.1 Å the parameters are given in Table 3.

TABLE 3

Parameters of the nearest coordination shells around Pt in crystalline cisplatin, saturated water solution of cisplatin and in liquid, frozen and freeze dried samples of liposome-encapsulated cisplatin.

| Pt neigh.[a] | N[a] | R(Å)[a] | $\sigma^2(Å^2)$[a] | Fit r-factor[c] |
|---|---|---|---|---|
| *Crystalline cisplatin* | | | | |
| N  | 2.0(2)[b] | 2.052(4) | 0.0022(9) | 0.007 |
| Cl | 2.0(2)    | 2.330(1) | 0.0025(3) |       |
| Pt | 2.0(5)    | 3.37(2)  | 0.016(3)  |       |
| *Cisplatin dissolved in water* | | | | |
| N  | 2.3(4) | 2.02(1) | 0.002(1) | 0.006 |
| Cl | 1.9(2) | 2.29(1) | 0.003(1) |       |
| *Liposome-encapsulated cisplatin: liquid* | | | | |
| N  | 2.2(4) | 2.01(1) | 0.002(1) | 0.017 |
| Cl | 2.3(3) | 2.29(1) | 0.003(1) |       |
| *Liposome-encapsulated cisplatin: frozen* | | | | |
| N  | 2.4(4) | 2.00(1) | 0.002(1) | 0.022 |
| Cl | 2.2(3) | 2.29(1) | 0.003(1) |       |
| *Liposome-encapsulated cisplatin: freeze-dried* | | | | |
| N  | 1.9(3) | 2.03(1) | 0.002(1) | 0.005 |
| Cl | 2.2(3) | 2.32(1) | 0.003(1) |       |

[a]Abbreviations: type of neighbor atom, N = number, R = distance, $\sigma^2$ = Debye-Waller factors
[b]Uncertainty of the last digit is given in parentheses.
[c]Fit r-factor as a measure of goodness of fit is given in the last column (Stern, E. A., et al., Physica B 208, 209: 117, (1995)).

The crystalline sample, with its well-defined nearest neighbors, can also be used to determine another parameter, the amplitude reduction factor $S_0^2$ of the EXAFS signal for Pt atom. This number is transferable between different samples with the central atom in a similar chemical (valence, coordination) state. The result ($S_0^2 = 0.77 \pm 0.03$) is in good agreement with theoretical estimates [Roy, M., et al., *J. Phys. IV France* 7:C2-151-C2-152 (1997)] and is used in the analysis of subsequent cisplatin samples.

Figure 10:
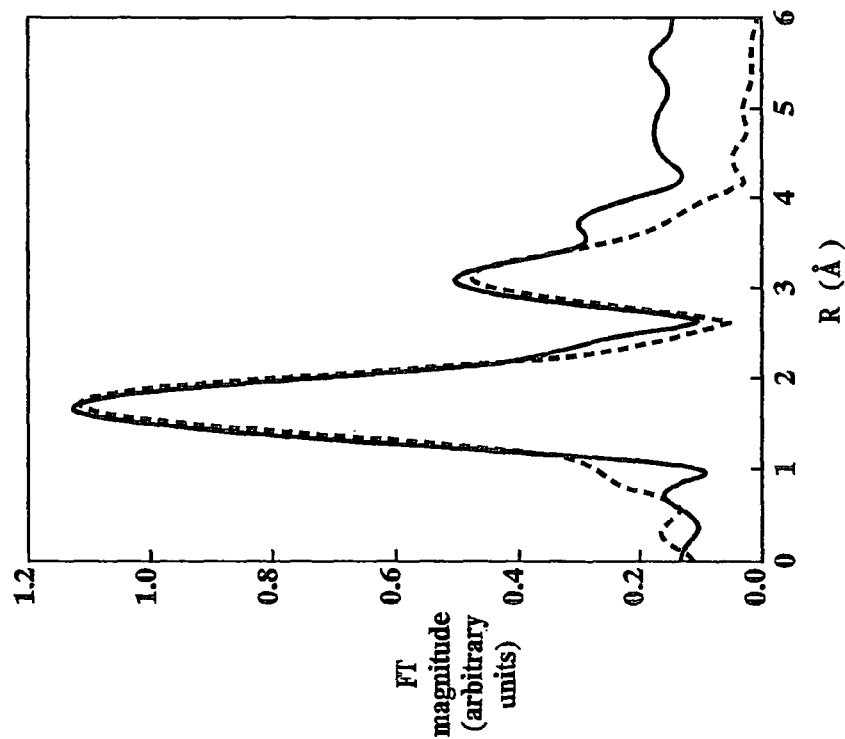
FIG. 10 is the $k^2$-weighted Fourier transform of the EXAFS spectrum of cisplatin dissolved in water; with the same notation as in FIG. 9.

The FT spectrum of the saturated aqueous solution of cisplatin shown in FIG. 10 is another, possibly closer, template for identification of the Pt atom neighborhood in the encapsulated samples. The comparison with the crystalline cisplatin shows a remarkable similarity in all details up to the distance of 3.5 Å. The model of the Pt neighborhood is thus based on the closest shell of 2 N and 2 Cl atoms of the molecule, as in the crystalline sample. A very good fit (Table 3) is obtained for the interval from 1.1 to 2.5 Å, with model parameters identical to those of the crystalline sample within error interval. The higher-order scattering contributions from the same shell extend the validity of the model up to 4 Å, providing the explanation of the small double peak within the region. The presence of Pt atom neighbors at a larger distance, such as confirmed in the crystalline sample, is completely excluded by the fit. The opposite finding would point to aggregation of the cisplatin molecules in the solution which, if true, should certainly have been known from physico-chemical data (osmotic pressure, freezing-point depression). Among conceivable expansions of the basic closest-neighbor model, the only one supported by the data is a large diffuse shell of O atoms. Apparently, it describes the hydration shell of the molecule. Its parameters, subject to strong intercorrelation, cannot be determined with satisfactory precision. The important point, however, is that it does not extend inwards to the immediate vicinity of the central Pt atom.

Figure 11:
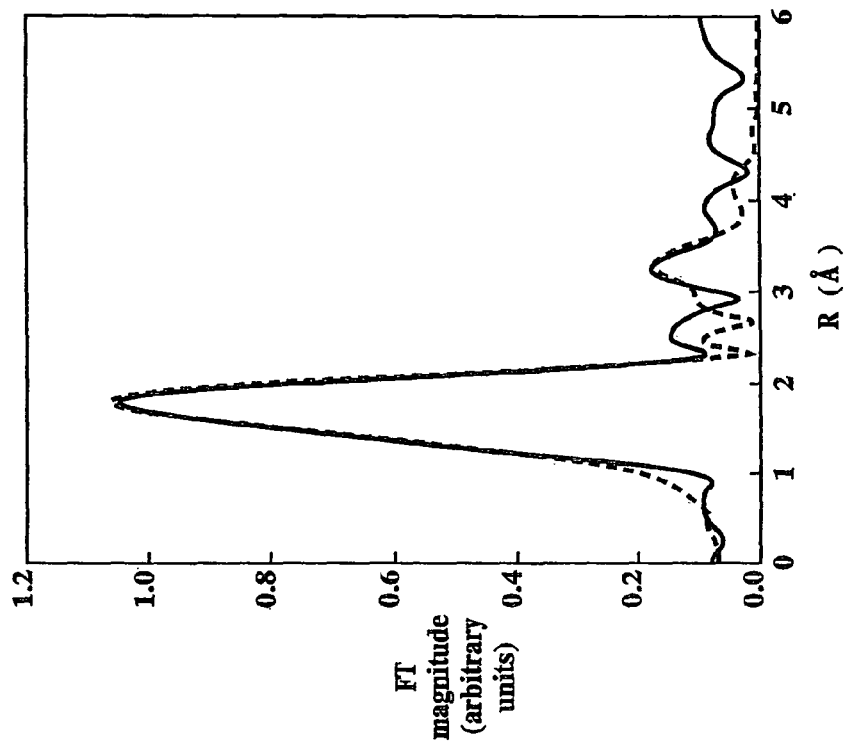
FIG. 11 is the $k^2$-weighted Fourier transform of the EXAFS spectrum of liquid sample of liposome-entrapped cisplatin; with the same notation as in FIG. 9.
Figure 12:
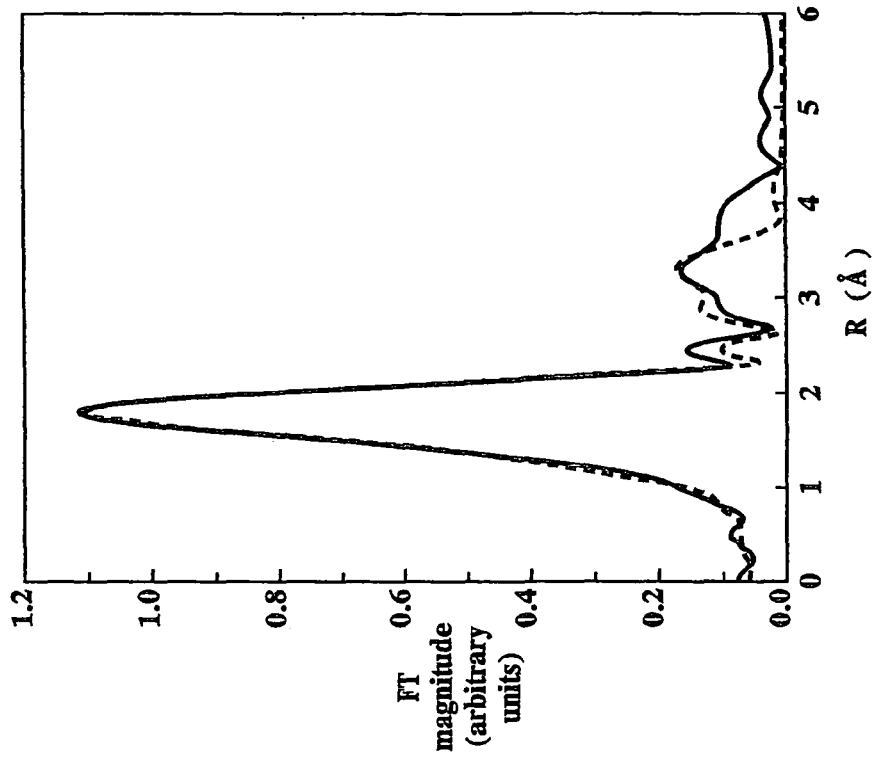
FIG. 12 is the $k^2$-weighted Fourier transform of the EXAFS spectrum of frozen sample of liposome-entrapped cisplatin; with the same notation as in FIG. 9.
Figure 13:
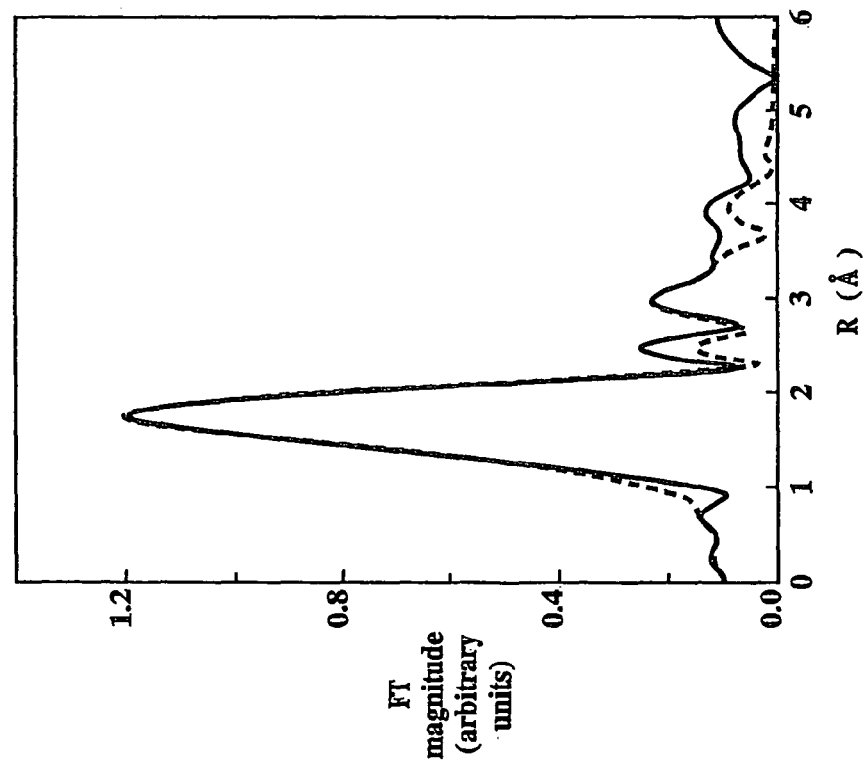
FIG. 13 is the $k^2$-weighted Fourier transform of the EXAFS spectrum of freeze-dried sample of liposome-entrapped cisplatin; with the same notation as in FIG. 9.

The spectra of the three samples of encapsulated cisplatin shown in FIGS. 11-13 (liquid, frozen and freeze-dried, respectively), although considerably more noisy, agree perfectly with that of the cisplatin solution in k- as well as in r-space. The quantitative analysis in the R interval from 1.1 Å to 2.5 Å confirms this observation (Table 3). The presence of the second-shell Pt atom neighbors is again excluded, so that aggregation of encapsulated cisplatin molecules is not indicated. The vestigial contribution of the hydration shell is occluded by the noise.

The determination of the crystal structures in the neighborhood of the Pt atom does not only help to determine the aggregation state but can also shed light on its chemical structure and consequently, chemical stability. The first neighbors of the Pt atom, the directly bonded Cl and N atoms are found at the unchanged distance and coordination number in all samples which show that the cisplatin molecule is not appreciably affected by the physical state of the system.

The observation of two N and two Cl atoms in the first coordination shell demonstrates that the encapsulated cisplatin molecules are chemically stable and do not hydrolyze, i.e. exchange one or two Cl atoms with water. This is an important observation because it can be obtained directly from the unperturbed sample while other analyses of such complex and subtle systems may lead to chemical and physical changes during sample preparation.

The absence of Pt neighbors at 3.37 Å of the Pt atom clearly demonstrates that the cisplatin solution inside the liposomes does not crystallize. To be more specific, it does not crystallize in the modification of the crystalline sample [Milburn, G. H. W., et al., *J. Chem. Soc. A. JCSIA*, p. 1609 (1966); Moeller, M., et al., *Curr. Op. Cooo. Inteff. Sci.* 2:177-187 (1997)]. However, another crystal modification of cisplatin is known [Milburn, G. H. W., et al., *J. Chem. Soc. A. JCSIA*, p. 1609 (1966)]. It is hydrated cisplatin in which the closest Pt neighbors are removed to a distance beyond 4 Å, on behalf of interposed water molecules which contribute two O neighbors to each Pt atom at the distance of 2.03 Å [Kuroda, R., et al., *Inorganic Chemistry* 22:3620 (1983); Faggiani, R., et al., *Canadian Journal of Chemistry* 60:529 (1982)]. Neither the encapsulated samples nor even the plain solution show O atoms so close to the central Pt. Therefore formation of hydrated crystal structure liposomes is also excluded.

EXAFS results are supported by extensive absorption studies of the drug to lipid bilayers, which have shown that cisplatin does not absorb onto phosphatidylcholine bilayers [Speelmans, G., et al., *Biochim. Biophys. Acta* 1283:60 (1996)]. Additionally, [195]Pt NMR studies of the same system did not show any line broadening and all the Pt signal could be attributed to the narrow isotropic signal of rapidly rotating drug also characterized in free drug solution.

Frozen and freeze dried liposomal sample are similar to the liquid one. The data in Table 3 show that neither freezing nor freeze drying induce drug crystallization. This is consistent with the fact that water in pores (<200 nm) of comparable size to the liposome interior does not behave like bulk water. Properties such as freezing and melting are affected by the large surface to volume ratio for encapsulate water molecules and it may simply freeze into a glassy state without crystallizing out solutes [Holly, R., et al., *J. Chem. Phys.* 108:4183 (1998)].

The data shown above, as well as NMR observations, suggest that cisplatin in the liposome interior forms a supersaturated solution. Depending on the liposome size, typically between 1000-3000 drug molecules are entrapped. In this study, from the liposome size, and lipid and drug concentrations it is reasonable to estimate that each liposome contains on average around 3000 cisplatin molecules. Assuming a molecular volume of 60 Å[3] for each cisplatin molecule, the size of a hypothetical crystal these molecules would form upon precipitation can be calculated. If the molecules would associate into a solid cube, its side would be 55-60 Å.

While not intending to be bound to any particular theory, one explanation for the above observations is that the number of compartmentalized molecules may be simply too small to permit crossing the energy barrier from crystal embryo to real crystal. So, the encapsulated cisplatin molecules are constantly associating into crystallization nuclei and because there are not enough molecules to overcome the barrier to start crystallization, the aggregates constantly disassociate. This would be an example of a "frustrated system" because the compartmentalization of molecules and their small number and (small) size prevent them from achieving a stable thermodynamic equilibrium.

It will be appreciated that the phenomena of a supersaturated compound in a liposome will find use in fields other than drug delivery. For example, applications where a high concentration of an agent is required on demand, such as reaction kinetics, would benefit from a method to maintain a high concentration of a compound ready for use. Other areas of use include diagnostic kits or storage means for proteins and peptides.

III. EXAMPLES

The following examples further illustrate the invention described herein and are in no way intended to limit the scope of the invention.

Example 1

Preparation of Liposomes Containing Cisplatin

A. Step 1: Drug Solution Preparation

Sterile water was heated to 63-67° C. in a TEFLON-lined pressure vessel and sodium chloride (0.9%) was added. Cisplatin was added at a concentration of 8.5 mg/ml and mixed until dissolved, approximately 15-25 minutes.

B. Step 2: Lipid Dissolution 257.0 g PEG-DSPE, 719.4 g HSPC and 308.4 g cholesterol (molar ratio of 50.6/44.3/5.1) were added to 900 ml dehydrated ethanol at 60-65° C. and mixed until dissolved, approximately 2 hours. The dissolved lipids were added to 7670 g of drug solution to give a total lipid concentration of approximately 150 mg/ml.

C. Step 3: Lipid Hydration/Drug Loading

The warm lipid solution was rapidly added to the warm (63-67° C.) drug solution, with mixing, to form a suspension of liposomes having heterogeneous sizes. The suspension was mixed for one hour at 63-67° C. The cisplatin concentration in the hydration mixture was 7.2 mg/ml and, at this stage, approximately 30% of the drug was encapsulated in the liposomes. 10% of the total solution volume was ethanol and the total lipid concentration was 150 mg lipid/ml.

D. Step 4: Extrusion

The liposomes were sized to the desired mean particle diameter by controlled extrusion through polycarbonate filter cartridges housed in Teflon-lined stainless steel vessels. The liposome suspension was maintained at 63-65° C. throughout the extrusion process, a period of 6-8 hours.

E. Step 5: Low-Grade Filtering

After sizing, the liposome suspension was cooled to room temperature (20-25° C.) and filtered through a 1.2 μm 142-mm Gelman Versapor filter (acrylic copolymer on a Nylon 66 support) to remove precipitated drug. At this stage approximately 50% of the drug was encapsulated.

F. Step 6: Diafiltration

A sucrose/sodium chloride solution was prepared by dissolving sucrose (100 mg/ml) and sodium chloride (0.058 mg/ml) in sterile water. The pH of the solution was adjusted to approximately 5.5 with 2 N HCl or NaOH. The solution was filtered through a 0.22 μm Durapore filter.

The liposome suspension was diluted in approximately a 1:1 (v/v) ratio with the sucrose/sodium chloride solution and diafiltered through a polysulfone hollow-fiber ultrafilter. Eight volume exchanges were performed against the sucrose/sodium chloride solution to remove the ethanol and unencapsulated drug. The process fluid temperature was maintained at about 20-30° C. Total diafiltration time was approximately 4.5 hours.

The liposome suspension was then concentrated to approximately 1.2 mg cisplatin/ml by ultrafiltration. The post diafiltration process fluid was analyzed for cisplatin content by HPLC. The liposomes had an internal phase of 8.5 mg/ml cisplatin in 0.9% sodium chloride and an external phase of sucrose/sodium chloride solution.

G. Step 7: Dilution

A diluent was prepared by dissolving histidine (10 mM) in a sucrose/sodium chloride (10% sucrose/1 mM NaCl) solution to a target histidine concentration of 1.55 mg/ml in the final mixture. The liposome suspension was diluted to a target cisplatin concentration of 1.05 mg/ml with the histidine diluent. The pH of the suspension was adjusted to 6.5 with 2N NaOH or HCl.

H. Step 8: Sterile Filtration

The liposome suspension was heated to 33-38° C. and filtered through a 0.2 μm Gelman Supor polyethersulfone filter. Total filtration time was approximately 10 minutes.

Example 2

NMR Analysis

A. Preparation and Characterization of $^{15}$N-labeled Cisplatin [cis-PT($^{15}$NH$_3$)$_2$Cl$_2$]

cis-$^{15}$N-diamminedichloroplatinum(II) (cisplatin) was synthesized according to the procedure described by Boreham, et al., Aust. J. Chem. 34:659 (1981). The product was characterized by both $^{195}$Pt NMR spectroscopy and by the thiourea test. Thiourea was added to an aqueous solution of the $^{15}$N-labeled cisplatin, and the solution was heated to 40-50° C. The appearance of a yellow color was indicative that the product was in the cis configuration, whereas the appearance of a colorless solution indicated the presence of the trans isomer. The cis-$^{15}$N-DDP was dissolved in DMF and analyzed by $^{195}$PtNMR.

B. Preparation of Liposomes Containing Cisplatin

Initial $^{195}$PtNMR measurements were carried out using $^{2000}$PEG-DSPE [polyethylene-glycol (M.W. approximately 2000)-derivatized distearoyl-phosphatidyl-ethanolamine], cholesterol, large unilamellar liposomes, with 99 mg/ml total lipids, 78 mM=2.40 mg/ml P, containing 1.64 mg/ml Pt.

1. Preparation of $^{15}$N-cisplatin Encapsulated in Sterically-Stabilized Liposomes 8.5 mg/ml $^{15}$N-labeled cisplatin was dissolved in 0.9% NaCl at 65° C. and left at this temperature for 1 hour. Lipids (HSPC/cholesterol/$^{2000}$PEG-DSPE 51:44:5) were dissolved in ethanol. The lipids were hydrated by adding this ethanolic solution to the drug mixture. Final lipid concentration was 150 mg/ml (15%) in 10% ethanol, at 65° C. The mixture was kept stirring for 1 hour at 60° C., then extruded at 65° C. through 100 nm and 200 nm pore size polycarbonate filters using the Lipofast syringe extruder. Sized liposomes (~100 nm) were allowed to cool to room temperature. During the cooling, a heavy yellow precipitate formed. The supernatant was collected and allowed more standing-time at room temperature. More precipitation occurred, and the supernatant was collected again. The sample was diluted twofold and dialyzed 5 times against 100 volumes of 10% sucrose containing 1 mM NaCl at room temperature. Under these conditions, a complete equilibration with 10% sucrose containing 1 mM NaCl should occur. Finally, histidine buffer (pH 6.5) was added to a final concentration of 10 mM. The final liposome dispersion was translucent, white. Aliquots of the liposomes and of both precipitates were analyzed by heteronuclear single quantum coherence (HSQC) at 30° C.

2. Sample Preparation for HSQC Experiments

The $^{15}$N-cisplatin was dissolved in either 0.9% NaCl or in 10% sucrose (8.5 mg/ml), at 65° C. Control samples, without cisplatin, were prepared and processed according to the same procedures. After cooling, histidine buffer (10 mM, pH=6.5) was added. Treated samples were stored at 4° C. or at (−20)° C.

C. NMR Measurements

1. $^{195}$PtNMR $^{195}$PtNMR measurements were carried out on a Varian VXR-300S spectrometer with a 7.05 T magnet equipped with a 5-mm computer switchable probe. The platinum chemical shifts were measured relative to the external reference signal of $K_2PtCl_4$ set at −1624 ppm. Data were collected with and without broad-band decoupling of the protons, using 100.0 kHz spectral width, acquisition time of 0.010 s. Usually, 350,000 pulses or more were acquired and a line broadening of 300 Hz was applied. The samples were measured, without spinning, at 37° C. and 60° C. A capillary containing 2 mg/ml ($4.82 \times 10^{-3}$M) $K_2PtCl_4$ was added to the NMR tubes as an internal reference of a known concentration. The data were apodized using a line broadening equal to the natural line width (in Hz) prior to processing and integration.

2. $^{31}$P NMR $^{31}$P measurements were carried out at room temperature and at 60° C. using a 5 mm computer-switchable probe. The $^{31}$P chemical shifts were measured relative to phosphoric acid set at 0 ppm. Data were collected with broad-band decoupling of the protons, using 10000 Hz spectral width, and an acquisition time of 1.6 s. Usually, 250 pulses or more were acquired and a line broadening of 20.0 Hz was applied. Placebo (control) and cisplatin-loaded liposomes were studied by $^{31}$P NMR. The liposomes contained large unilamellar vesicles (LUV) and were composed of hydrogenated phosphatidylcholine (HPC), cholesterol, and $^{2000}$PEG-DSPE at a mole ratio of 55:40:5. Samples were prepared by mixing 700 μl of the original liposome sample with 70 μl of $D_2O$.

3. HSQC NMR Measurements

All [$^1$H, $^{15}$N] HSQC data were obtained using a Bruker DXR 400 MHz NMR spectrometer, equipped with a 5 mm multinuclear inverse detection probe. The 2D data were recorded using Bruker sequence of INVIGSTP (inverse detection 2D $^1$H-X correlation via double INEPT transfer, phase sensitive using TPPI with decoupling during acquistion). $^{15}$N spins were irradiated during the acquisition time using the GARP-1 sequence. The $^{15}$N chemical shifts were externally referenced to 1.5 M $NH_4Cl$ in 1M HCl: $^1$H chemical shifts were externally referenced to TSP ($Me_3Si(CD_2)_2CO_2Na$). 2-8 transients were acquired, using an acquisition time of, 0.251 s. spectral widths of 2 KHz in both $f_2$ and $f_1$ dimensions, and 256 increments of $t_1$. All spectra were acquired at 300° K. (27° C.). Spectra were collected in approximately 20 minutes and the data were processed using Bruker software, with no line broadening.

4. Quantification of Platinum Content by $^{195}$PtNMR $K_2PtCl_4$ was chosen as an internal reference since it is a stable compound whose chemical shift (−1624 ppm) is in close proximity to that of cisplatin (−2100 ppm), yet is distant enough to avoid overlapping. The $K_2PtCl_4$ (2 mg/mL, 4.82 mM), was sealed in a capillary, and concentrated hydrochloric acid was added to prevent its hydrolysis. The capillary was inserted into the 5 mm NMR tube containing the sample, and the $^{195}$Pt NMR spectrum was acquired as described above.

To test the method's accuracy, three cisplatin samples of varying concentrations (1.54, 2.0, and 2.31 mg/ml) were measured in the presence of the capillary at 37° C. The areas under the curves were integrated relative to the area under the reference peak, and the elemental platinum concentration was calculated. To verify the calculated figures, atomic absorption (AA) measurements were performed.

5. Atomic Absorption Spectroscopy

Atomic absorption measurements were performed on a Varian SpectrAA Zeeman 300 spectrometer. The platinum concentration was calculated according to a calibration curve of a known concentration of a $K_2PtCl_4$ stock solution (250 ng/ml, $6.02 \times 10^{-7}$M).

Example 3

EXAFS Analysis

A. Liposome Preparation

1. Materials

Cholesterol (CH) from Croda, Fullerton, Calif.; Hydrogenated Soy Phosphatidylcholine (HSPC) from Lipoid, Ludwigshafen, Germany; N-Carbonyl-methoxypolyethylene glycol 2000)-1,2-distearoyl-sn-glycerophosphoethanolamine sodium salt (MPEG-DSPE) from Sygena, Liestal, Switzerland. Cisplatin (USP grade, not less than 98% pure) from Heraeus GmbH, Hanau, Germany.

2. Liposome Preparation

Liposome-encapsulated cisplatin was prepared as described in Example 1, where multilamellar vesicles were formed by injection of ethanolic lipid solution into drug solution at 65° C., followed by cooling and dialysis. The liposomal lipid composition was HSPC/CH/MPEG-DSPE in a molar ratio of 51:44:5. The cisplatin concentration was 1.1 mg/ml and the drug encapsulation, as determined by gel-exclusion chromatography, was 98%. Total lipid concentration was 118 mM and mean particle diameter was 106 nm, determined by dynamic laser-light scattering (Coulter model N4MB, Miami, Fla.). The encapsulated cisplatin was dissolved in 0.9% (w/v) NaCl solution and the liposomes suspended in an aqueous phase of 0.9% NaCl solution, 10 mM histidine, pH 6.5.

Placebo liposomes were made identically to cisplatin liposomes, but contained no drug. The placebo liposomes had a mean particle diameter of 101 nm and a total lipid concentration 73 mM.

Freeze-dried cisplatin liposomes were prepared as follows. A sample of cisplatin-containing liposomes was dialysed using molecular weight cut-off 14,000 dialysis tubing and four, twenty-volume exchanges of 10% (w/v) sucrose solution over twelve hours at room temperature. The resulting liposome suspension in 10% sucrose solution was then rapidly frozen using a dry-ice/isopropanol mixture and lyophilized overnight at high vacuum (100 mTorr).

B. EXAFS Measurements

Platinum $L_3$-edge EXAFS spectra of the samples were measured in a transmission mode at the x-ray beamline ROEMO2 (X1.1) in Hamburger Synchrotronstrahlungslabor HASYLAB at Deutschen Elektronen-Synchrotron DESY (Hamburg, Germany). A Si(311) fixed-exit double-crystal monochromator was used with 2 eV resolution at 12 keV. Harmonics were effectively eliminated by detuning the monochromator crystal using a stabilization feedback control. Ionization cells filled with argon at 1 bar were used to detect incident and transmitted flux of the monochromatic x-ray beam through the sample. The absorption spectra were recorded as a function of the x-ray photon energy with an integration time of 1 s/point. Standard stepping progression within a 1000 eV region above the edge was adopted.

Liquid, frozen and freeze dried liposome-encapsulated cisplatin samples and a water solution of cisplatin were prepared in a variable-length liquid absorption cell with KAPTON™ windows. Due to the very low concentration of Pt in the samples, the optimum absorption thickness was found with a 5 mm thick layer of the liquid samples and a 2 mm layer of the freeze dried sample. The obtained $PtL_3$ edge jump was only 0.04 and 0.1 for liposome encapsulated samples and for aqueous solution respectively at the total absorption thickness of 2. Ten experimental runs were superimposed to improve the signal to noise ratio. A reference spectrum was taken on a 5 mm thick layer of an aqueous solution of empty liposomes. Powdered crystalline sample was prepared on multiple layers of adhesive tape, with the edge jump of about 1. A reference spectrum was measured on empty tapes.

The complete disclosures of the patents, patent documents, and publications cited herein are incorporated by reference in their entirety as if each were individually incorporated. Various modifications and alterations to this invention will become apparent to those skilled in the art without departing from the scope of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

It is claimed:

1. A method for preparing liposomes having an entrapped compound in the form of a supersaturated solution, comprising:
    selecting a compound of low-lipophilicity having room temperature water solubility capable of exhibiting at least a two-fold increase in response to a condition selected from the group consisting of: (i) increasing solvent temperature, (ii) adding a co-solvent, and (iii) changing solvent pH;
    preparing from a supersaturated solution of the compound liposomes at selected size intervals;
    analyzing by a combination of NMR spectroscopy and atomic absorption spectroscopy said liposomes for the presence or absence of precipitated compound within the liposomes; and
    based on said analyzing, selecting liposomes of a size that corresponds to liposomes having no entrapped precipitated compound.

2. The method of claim 1, wherein selecting the liposomes comprises selecting liposomes that have a liposome size of between about 60 nm to about 1000 nm.

3. The method of claim 1, wherein preparing the liposomes comprises preparing liposomes at size intervals between about 60 to about 1000 nm.

4. The method of claim 1, wherein preparing the liposomes comprises preparing liposomes at size intervals between about 70 nm to about 500 nm.

5. The method of claim 1, wherein said preparing liposomes comprises preparing a solution of lipids.

6. The method of claim 5, wherein the preparing comprises preparing a solution of lipids that comprises a lipid derivatized with a hydrophilic polymer.

7. The method of claim 6, wherein the preparing comprises preparing a solution of lipids effective to form a rigid lipid bilayer.

8. The method of claim 1, further comprising removing from an external liposome suspension medium the condition selected to maintain the compound above its room temperature solubility.

9. A method for preparing liposomes which contain a supersaturated solution of a compound of low-lipophilicity and low aqueous solubility at room temperature, comprising:
    preparing an aqueous supersaturated solution of the compound;
    hydrating a lipid film or a lipid solution with said supersaturated solution of the compound to form liposomes;
    sizing the liposomes to selected sizes;
    analyzing by a combination of NMR spectroscopy and atomic absorption spectroscopy the liposomes at each size for the presence or absence of precipitated compound within the liposomes; and based on said analyzing, selecting liposomes having a size that corresponds to liposomes having no precipitated compound.

10. The method of claim 1, wherein the compound is cisplatin.

11. The method of claim 9, wherein the compound is cisplatin.

* * * * *